United States Patent [19]
Isbell et al.

[11] Patent Number: 6,022,982
[45] Date of Patent: Feb. 8, 2000

[54] METHOD FOR THE DEVELOPMENT OF δ-LACTONES AND HYDROXY ACIDS FROM UNSATURATED FATTY ACIDS AND THEIR GLYCERIDES

[75] Inventors: Terry A. Isbell, Elmwood; Steven C. Cermak, Galesburg, both of Ill.

[73] Assignee: The United States of America as represented by the Secretary of Agriculture, Washington, D.C.

[21] Appl. No.: 09/211,017

[22] Filed: Dec. 14, 1998

Related U.S. Application Data

[63] Continuation-in-part of application No. 08/534,810, Sep. 27, 1995.

[51] Int. Cl.⁷ .................................................. C07D 309/00
[52] U.S. Cl. ........................... 549/273; 554/161; 568/876
[58] Field of Search ........................... 554/161; 568/876; 544/273

[56] References Cited

PUBLICATIONS

Isbell, Terry A. and Plattner, Beth A., "A Highly Regioselective Synthesis of δ–Lactones from Meadowfoam Fatty Acids", *JAOCS*, vol. 74, No. 2, 1997, pp. 153–158.

Nakano, Y. and Foglia, T.A., "Methanesulfonic Acid Catalyzed Addition of Aromatic Compounds to Oleic Acid", *JAOCS*, vol. 61, No. 3, Mar. 1984, pp. 569–573.

Isbell, Terry A. and Kleiman, Robert, "A Highly Regioselective Synthesis of Eicosanolactone and Docosanolactone from Meadowfoam Seed Oil; Utilization of the Unique Chemical Structure of a New Crop's Fatty Acids", *Abstract*, 21st World Congress and Exhibition of the International Society for Fat Research (ISF), Oct. 1–5, 1996, The Hague, The Netherlands.

Showell, John S., et al., "Perchloric Acid Isomerization of Oleic Acid", J. Amer. Oil Chemists Soc., 36, 1959, p. 343.

*Primary Examiner*—Deborah D Carr
*Attorney, Agent, or Firm*—M. Howard Silverstein; Randall E. Deck; John D. Fado

[57] ABSTRACT

An improved process for the production of high yields of δ-lactones and 5-hydroxy fatty acids from unsaturated fatty acids such as oleic acid is disclosed. The δ-lactones may be produced by reacting one or more $\Delta^9$ to $\Delta^{15}$ unsaturated fatty acids in the presence of an acid catalyst and at a temperature between about 20 to 70° C. Moreover, yields of the δ-lactones may be increased even further by reaction in the presence of dipolar, non-participating, non-aqueous solvents. The unsaturated fatty acids may be free or esterified with glycerol or other aliphatic alcohols, and the δ-lactones may be produced by reacting mono-, di- or triglycerides of the unsaturated fatty acids with the same catalysts. Because the δ-lactones may be produced from the triglycerides of unsaturated fatty acids, the instant process may be practiced using naturally occurring plant oils directly, without the need for any preliminary steps of saponification or steam splitting. Optionally, the δ-lactones so formed may be further reacted to produce 5-hydroxy fatty acids. These 5-hydroxy fatty acids may be produced by reaction of the δ-lactones with an alkali in an aqueous solution.

24 Claims, No Drawings

METHOD FOR THE DEVELOPMENT OF δ-LACTONES AND HYDROXY ACIDS FROM UNSATURATED FATTY ACIDS AND THEIR GLYCERIDES

CROSS-REFERENCE TO RELATED APPLICATIONS

This application is a continuation-in-part of U.S. patent application Ser. No. 08/534,810, filed Sep. 27, 1995, the contents of which are incorporated by reference herein.

BACKGROUND OF THE INVENTION

1. Field of the Invention

This invention relates to a novel process for producing δ-lactones and 5-hydroxy fatty acids from unsaturated fatty acids and their glycerides.

2. Description of the Prior Art

Gamma stearolactones and other small chain γ-lactones have been used as greases, antioxidants, perfumes, food flavors and dispersants for motor fuels. Techniques for the synthesis of both δ- and γ-lactones have been described throughout the chemical literature, and have included acid catalyzed reactions of unsaturated or olefinic acids.

Showell et al. (1968, J. Org. Chem., 33:2697–2704) disclosed a process for the production of γ-stearolactone from oleic acid (18:1 $\Delta^9$) by perchloric acid catalysis. Small amounts of δ-lactone intermediates were identified in the reaction mixture. Reactions using other fatty acids, namely undecylenic acid (11:1 $\Delta^{10}$) and erucic acid (22:1 $\Delta^{13}$) also produced γ-lactones under the same optimum conditions used for oleic acid (page 2702, paragraph 2).

The addition reaction of aromatic compounds to oleic acid was disclosed by Nakano and Foglia (1984, JAOCS, 61:569–573). Reaction of oleic acid with a participating aromatic solvent and a methanesulfonic acid catalyst produced ring substituted fatty acids (phenyl stearate) as well as small amounts of δ-lactone (δ-stearolactone). Interestingly, the authors reported that the use of monochlorobenzene as solvent favored the production of δ-lactones over the addition products.

High yields of δ-lactones have been achieved by the acid catalyzed reaction of substituted 4-hexenoic acid containing a carbocation stabilizing functionality as described by Fujita et al. (1982, J. Chem. Tech. Biotechnol., 32:476–484). See Table 3.

Ansell and Palmer (1963, J. Chem. Soc., p. 2640–2644) described the production of γ- and δ-lactones from unsaturated five to eight carbon alkenoic acids in an acid or acidic solvent, using high molar equivalents of $H_2SO_4$ or trifluoroacetic acid ($CF_3CO_2H$) catalyst. In those trials where the proportion of δ-lactones was high (the ratio of δ to γ was high), yields were significantly reduced.

More recently, Isbell and Plattner (1997, JAOCS, 74:153–158) disclosed a process for the production of δ-lactones from $\Delta^5$ unsaturated fatty acids such as eicosenoic acid found in meadowfoam oil. Selective synthesis of δ-lactones was accomplished by reaction of the $\Delta^5$ fatty acid in a highly polar solvent in the presence of an acid catalyst at low temperatures. Selectivity for the δ-lactone over the γ-lactone was favored by using lower temperatures, low acid concentrations, and high solvent ratios.

Unsaturated fatty acids have been disclosed as starting materials for the production of other commercially valuable products as well. For instance, unsaturated fatty acids have been used for the production of dimer acids by a variety of techniques, including clay catalyzed reactions, as reviewed by Johnson ["Dimerization and Polymerization," in: Fatty Acids, E. H. Pryde (ed.), AOCS, (1979), pages 343–352] and Leonard [in: Encyclopedia of Chemical Technology, Kirk-Othmer, John Wiley & Sons, third edition, volume 7, (1979)]. Burg et al. (U.S. Pat. No. 5,380,894, issued Jan. 10, 1995) disclosed a process for the production of estolides from unsaturated fatty acids in the presence of water and a clay catalyst. Burg et al. further disclosed hydrolyzing the estolides to form hydroxy fatty acids, which are useful as lubricants and greases, and in cosmetics, soaps, detergents, and fabric softeners.

SUMMARY OF THE INVENTION

We have now invented an improved process for the production of high yields of δ-lactones and 5-hydroxy fatty acids from unsaturated fatty acids which are either free or esterified. Surprisingly, the δ-lactones may be produced in high yield by reacting one or more $\Delta^9$ to $\Delta^{15}$ unsaturated fatty acids in the presence of an acid catalyst and at a temperature between about 35 to 70° C. Moreover, yields of the δ-lactones may be increased even further by reaction in the presence of dipolar, non-participating, non-aqueous solvents. The unsaturated fatty acids may be free or esterified with glycerol or other aliphatic alcohols, and the δ-lactones may be produced by reacting mono-, di- or triglycerides of the unsaturated fatty acids with the same catalysts. Because the δ-lactones may be produced from the triglycerides of unsaturated fatty acids, the instant process may be practiced using naturally occurring plant oils directly, without the need for any preliminary steps of saponification or steam splitting. Optionally, the δ-lactones so formed may be further reacted to produce 5-hydroxy fatty acids. These 5-hydroxy fatty acids may be produced by reaction of the δ-lactones with an alkali in an aqueous solution.

In accordance with this discovery, it is an object of this invention to provide a method of making δ-lactones in high yields.

It is another object of this invention to provide a method of making δ-lactones in high yields from $\Delta^9$ to $\Delta^{15}$ unsaturated fatty acids, including oleic acid.

It is yet another object of this invention to provide a method of making 5-hydroxy fatty acids in high yields.

A still further object of this invention is to provide a method for making δ-lactones and/or 5-hydroxy fatty acids directly from triglycerides of unsaturated fatty acids.

Other objects and advantages of this invention will become readily apparent from the ensuing description.

DETAILED DESCRIPTION

Using the process of this invention, δ-lactones and 5-hydroxy fatty acids may be formed from $\Delta^9$ to $\Delta^{15}$ unsaturated fatty acids (i.e. having a double bond between $\Delta^9$ and $\Delta^{15}$ inclusive). Preferred starting materials include but are not limited to free and esterified unsaturated fatty acids of the formula (I):

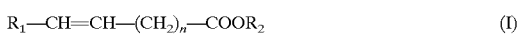

$$R_1\text{—CH=CH—}(CH_2)_n\text{—COOR}_2 \qquad (I)$$

wherein n is an integer between 7 and 13, particularly 7, 9 or 11, $R_1$ is hydrocarbon, particularly a $C_4$ to $C_{20}$ hydrocarbon, most preferably a $C_6$ to $C_{10}$ hydrocarbon, which may be saturated or unsaturated, and branched or straight chain, and $R_2$ is an H, an aliphatic hydrocarbon, or a glyceride moiety which in combination with the fatty acid comprises a mono-, di- or triglyceride. Examples of particularly preferred unsaturated fatty acids which may be used herein include free and esterified palmitoleic acid (16:1 $\Delta^9$), oleic acid (18:1 $\Delta^9$), linoleic acid (18:2, $\Delta^{9,12}$), erucic acid (22:1, $\Delta^{13}$), and linolenic acid (18:3, $\Delta^{9,12,15}$).

The $\Delta^9$ to $\Delta^{15}$ unsaturated fatty acids are naturally occurring in a variety of plant oils and may be conveniently obtained for use therefrom. Without being limited thereto, oils which may be used as sources, include soybean, cottonseed, corn, olive, peanut, palm, sesame, sunflower, canola, safflower, linseed, rice, crambe, high erucic rape, and high oleic canola oils.

As starting materials in the reaction of the invention, the unsaturated fatty acids may be provided in substantially pure form or, in the alternative, they may be provided as a mixture or in impure form. Moreover, although the starting unsaturated fatty acids may be free acids, the reaction may also be conducted using fatty acids which are esterified with aliphatic alcohols such as methanol, ethanol, isopropanol, or branched chain alcohols such as 2-ethyl hexanol or Guerbet alcohols, or with glycerol as mono-, di- or triglycerides, while retaining the production of $\delta$-lactones in high yields. Use of fatty acid triglycerides is particularly preferred. Because fatty acids occur predominantly as triglycerides in plant oils, the above-mentioned naturally occurring oils may be used directly in the reaction, thereby foregoing the need for any preliminary fatty acid isolation of the oil.

The practitioner skilled in the art will of course recognize that for products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Once the starting material has been selected, the free or esterified unsaturated fatty acids are reacted in the presence of an acidic catalyst under conditions suitable to form $\delta$-lactones. The catalyst, reaction temperature, and solvent are critical for production of the $\delta$ lactones in high yields. To a somewhat lesser extent, reaction yields are also effected by the concentration of the catalyst and solvent.

Although a variety of acids will catalyze the reaction of $\Delta^9$ to $\Delta^{15}$ to lactones, yields of $\delta$-lactones are relatively low. However, we have unexpectedly discovered that yields of $\delta$-lactones are greatly increased when using either concentrated $H_2SO_4$, methanesulfonic acid, or trifluoromethane sulfonic acid as catalyst. In contrast, yields are significantly reduced when using other acidic catalysts, including $HClO_4$. Without wishing to be bound by theory, it is believed that in the course of the reaction, $H_2SO_4$, methanesulfonic acid, and trifluoromethane sulfonic acid not only protonate the starting fatty acid, but also attack and effect the migration of the double bond down the hydrocarbon chain to the five position where the reaction to $\delta$-lactone may occur.

Reaction temperature is also critical for attaining high yields of $\delta$-lactones. Yields are significantly increased using a reaction temperature between about 35 to 70° C., particularly between about 40 to 70° C. Preferred temperatures for use herein are between about 40 to 70° C., particularly between about 40 to 50° C. Although the reaction may be conducted as low as room temperature (i.e. about 20° C.), reaction rates fall dramatically as the temperature is reduced below 35° C. In contrast, as the reaction temperature increases above 50° C., the selectivity for $\delta$-lactone over $\gamma$-lactone decreases, and a reaction temperature above 70° C. favors the production of $\gamma$-lactone rather than the $\delta$-lactone. The specific temperature selected will vary with pressure and the particular solvent selected, and the optimal temperature may be determined by routine experimentation.

In accordance with the preferred embodiment, the unsaturated fatty acids are provided in admixture with a solvent. Although its use is optional, the $\delta$-lactone yield and/or the ratio of $\delta$-lactones to $\gamma$-lactones in the product may be substantially increased if the reaction is conducted in the presence of a suitable solvent. Generally, maximum yields and $\delta/\gamma$ ratios are obtained using dipolar, non-participating, non-aqueous, solvents having a relatively high dielectric constant, $\xi_r$, greater than or equal to approximately 4.0 debyes, and preferably about 8 to 9 debyes. Solvents having a greater dielectric constant may be employed provided that the solvent does not participate in the reaction of the fatty acids. Suitable solvents for use herein include but are not limited to $CH_2Cl_2$, $CHCl_3$, and hydrocarbons such as hexane and cyclohexane, with $CH_2Cl_2$ and $CHCl_3$ being preferred. Aqueous and alcoholic solvents, as well as the aromatic solvents described by Nakano and Foglia (ibid) are participating solvents which significantly reduce reaction yields and thus are not suitable for use herein.

As mentioned above, the selection of the solvent for use herein, and specifically the boiling point of the solvent, may limit the functional reaction temperature, particularly for reactions conducted at atmospheric pressure. Solvents having higher boiling points are generally preferred to allow reactions to be conducted at atmospheric pressure within the above-described temperature ranges. Preferred solvents should therefore have a boiling point greater than or equal to about 35° C., more preferably greater than or equal to about 40° C., and particularly greater than or equal to about 70° C. It is understood however, that solvents having lower boiling points may be used and the reactions still conducted within the described temperature ranges, by use of pressurized reaction vessels.

The volume of the solvent used may also significantly effect the $\delta$-lactone yield and the ratio of $\delta$- to $\gamma$-lactones in the product, and should be between about 0 to 500% (measured as the volume of solvent relative to the weight of fatty acid). In the preferred embodiment, optimal yields and $\delta/\gamma$ ratios are attained using solvent concentrations between about 50 to 200%, particularly about 100%. Moreover, because the fatty acids possess relatively high boiling points, the use of lower solvent volumes (including 100%) allows the reaction mixture to be effectively superheated and thus the reaction may be conducted at higher temperatures beyond the solvents' normal boiling points. This is particularly advantageous when using solvents having relatively low boiling points such as $CH_2Cl_2$.

Conditions for $\delta$-lactone formation are selected to minimize the formation of $\gamma$-lactones (favoring a high $\delta/\gamma$ ratio in the product) while maximizing $\delta$-lactone yield. The catalyst should be present in a catalytically effective amount to produce $\delta$-lactones from the unsaturated fatty acids. Without being limited thereto, the suitable concentration of the catalyst may vary between about 0.5 to 10 molar equivalents, wherein a molar equivalent is defined herein as the moles of catalyst relative to the moles of starting fatty acids in the reaction mixture. However, in the preferred embodiment, the concentration of the catalyst should be between about 1.0 to 4.0 molar equivalents, particularly between about 1.0 to 2.0 molar equivalents.

The reaction mixture is preferably agitated throughout the course of the reaction, such as by moderate stirring, rocking, or inert gas bubbling, to ensure adequate contact of all components. The reaction may optionally be conducted with solvent reflux. The time for the reaction will vary with the starting materials, choice of catalyst, solvent and temperature. However, generally the reaction will be complete within 2 to 24 hours, usually within about 5 to 24 hours.

Using the process conditions described hereinabove, reaction yields of δ-lactones greater than 50%, preferably greater than 70%, have been obtained after reaction for 24 hours. Moreover, a high regioselectivity for δ-lactone relative to γ-lactone has also been obtained, with δ/γ ratios ranging from about 7:1 up to 30:1 following the same reaction.

The resultant δ-lactones may be represented by the general formula (II):

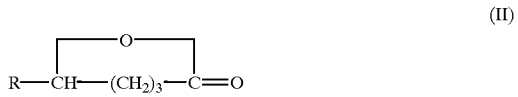

wherein R is a hydrocarbon which may be saturated or unsaturated, and branched or straight chain. Preferred δ-lactones include those formed by reaction of the above-mentioned $\Delta^9$ fatty acids, such as δ-stearolactone formed from oleic acid.

Following the reaction, the δ-lactones may be separated and recovered by solvent extraction. For example, δ-lactones may be extracted by addition of hexane, with residual water removed from the hexane layer by mixing over a drying agent. Pure δ-lactones may be subsequently recovered from the hexane phase by crystallization at about 0° C., or in the alternative by vacuum (0.001 torr) wiped film distillation at about 150° C.

The δ-lactones so-produced may be used as an emollient in cosmetics and moisturizing creams. It is also envisioned that, as with the γ-lactones, the δ-lactones will be useful as biodegradable lubricants and greases, antioxidants, perfumes, food flavors and dispersants for motor fuels. In addition to these direct applications, the δ-lactones may also be used as intermediates for the production of other commercially valuable compounds, including but not limited to 5-hydroxy wax esters, 5-hydroxy amides including ethanolamide derivatives, and particularly 5-hydroxy fatty acids.

Production of 5-hydroxy fatty acids may be readily accomplished by reaction of the δ-lactones in the presence of an alkali in an aqueous solution. Moreover, although the δ-lactones may be isolated prior to this reaction, in the alternative the reaction may be performed directly upon the reaction mixture resulting from δ-lactone formation, thereby obviating any intermediate steps of separation and purification of the δ-lactones. Following completion of the reaction of unsaturated fatty acids to δ-lactones, hereinafter referred to as the initial reaction, an aqueous solution of an alkali may be added and the reaction mixture held under conditions effective to form hydroxy fatty acids. The particular alkali employed is not critical, and virtually any hydroxy moiety containing base will be operable. Preferred alkali for use herein include alkali metal hydroxides such as KOH and NaOH. The amount of alkali added should be approximately 1.0 or greater moles in excess beyond the amount required to neutralize any acid catalyst remaining from the initial reaction.

To avoid interference in the production of hydroxy-fatty acids, any solvent from the initial reaction should be removed. While the solvent may be removed prior to addition of alkali, in the preferred embodiment it is removed concurrent with this reaction. Solvent removal may be effected, for example, by distillation during the course of the reaction. The vaporized solvent then may be collected in an overhead condenser operating without reflux. The temperature of the reaction should be between about 70 to 100° C. to maintain favorable reaction rates. The skilled practitioner will of course recognize that the temperature selected will vary with the solvent used in the initial reaction if it is to be removed by distillation.

The reaction may be terminated, generally in about 1 to 24 hours, by addition of an acid such as HCl or $CH_3COOH$ to quench or remove excess base. Sufficient acid should be added to lower the pH to between about 5 to 6, typically about 5.5. The 5-hydroxy fatty acids may be subsequently recovered in pure form from the reaction mixture by extracting into ethyl acetate after the pH is adjusted to approximately 5.5. Extraction into this solvent may require heating the ethyl acetate to reflux on a steam bath or other heat source to dissolve any precipitate. Excess water is removed and the organic phase dried over sodium sulfate or other suitable drying agents, filtered and allowed to cool to room temperature then finally in an ice bath. Vacuum filtration provides the hydroxy fatty acids in greater than 70% yield. Alternatively, the ethyl acetate extraction step may be avoided by direct filtration of the pH adjusted solution. Recovery in this manner will provide a higher yield of a slightly less pure fraction of hydroxy fatty acids.

The resultant 5-hydroxy fatty acids may be represented by the general formula (III):

wherein R is as described in formula (II). These hydroxy fatty acids may be used as biodegradable lubricants and greases, and in cosmetics, soaps, detergents, and fabric softeners.

As mentioned hereinabove, the δ-lactones may also be further reacted to produce hydroxy wax esters. In this embodiment, the δ-lactones are reacted with an alcohol in the presence of a catalytically effective amount of an acidic catalyst under conditions suitable to form hydroxy wax esters. A wide variety of organic alcohols may be reacted with the δ-lactones, including aromatic and normal or branched chain aliphatic alcohols. Hydroxy wax esters produced by reaction of a δ-lactone such as shown in formula (II) with an alcohol of the formula $R_2OH$, may be represented by the general formula (IV):

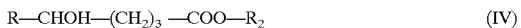

wherein $R_2$ is a hydrocarbon which may be saturated or unsaturated, branched or straight chain. As with the formation of 5-hydroxy fatty acids, this reaction may also be conducted using either δ-lactone which has been isolated or which remains in the initial reaction mixture.

Catalysts and conditions for production of hydroxy wax esters are similar to but not as restricted as those described for the production of the δ-lactones. Suitable catalysts include, for example, mineral acids, Lewis acids, clays and zeolites, with mineral acids such as $H_2SO_4$ and p-toluene sulfonic acid being preferred. The temperature for the reaction is not critical and may vary between about 20 to 150° C. Interestingly, when the reaction is conducted at higher temperatures, the amount of catalyst may be reduced or the catalyst may even be entirely omitted.

In the preferred embodiment, the 5-hydroxy wax esters are synthesized by mixing a slight excess of primary alcohol in the presence of about 0.01 equivalents of acid catalyst with δ-lactone (at the melting point of the lactone) and mixed thoroughly. An immediate precipitate will form and the whole reaction will solidify within about 15 minutes. At this point the reaction may be diluted in hexane and vacuum filtered to give near quantitative conversion of the δ-lactone to 5-hydroxy wax ester. Secondary, tertiary, hindered and other weaker nucleophilic alcohols will require longer reaction times and may not provide solid products.

Hydroxy wax esters produced in accordance with this invention may be used as moisturizers in cosmetics, biodegradable lubricants and dispersing agents for pigments and dyes in inks. Furthermore, the compounds possess strong surface active or chelating properties permitting their use as detergents and flocculants for heavy metals.

The δ-lactones may also be used to produce 5-hydroxy amides. The production of these compounds requires no catalyst to promote the reaction. Conversion takes place by mixing the δ-lactone with a slight excess of amine at the melting point of the δ-lactone. Primary amines provide an immediate precipitate upon addition of the amine signaling the completion of the reaction. Secondary, hindered and other weaker nucleophilic amines such as diethanol amine may require extended reaction times to reach completion. Upon consumption of the lactone, the reaction mixture may be diluted in hexane and vacuum filtered to remove any excess amine. This reaction may yield a near quantitative conversion to the 5-hydroxy amines.

The 5-hydroxy amides so produced may be useful as lubricants, cutting fluids, textile lubricants, hair care emollients, plasticizers and fabric softeners.

The following examples are intended only to further illustrate the invention and are not intended to limit the scope of the subject matter which is defined by the claims.

EXAMPLES

A series of reactions were conducted to examine the production of δ-lactones from oleic acid and its esters, or from erucic acid, and to examine the effects of different temperatures, catalysts and solvents (at different concentrations) on yields and δ/γ ratios. Ten g of the fatty acid was placed in a 100 ml reactor and equilibrated at the desired reaction temperature for 10 minutes. Reactions were run over a range of temperatures and using a variety of solvents, solvent concentrations, and catalyst concentrations as shown in Table 1. In some trials, no solvent was used. Concentrated $H_2SO_4$ or 70% $HClO_4$ were used as catalysts, and were added all at once to the reaction vessel in the molar equivalent amounts shown in Table 1, while stirring. Stirring was maintained throughout the course of the reaction. After 24 hours, the reaction was terminated by pouring into 50 ml of 50:50 hexane/ethyl octane and washed twice in 5 ml of 0.5 M $Na_2HPO_4$. The residual water was removed from the hexane layer by mixing over a drying agent and then filtered and concentrated in vacuo. The δ-lactone yields and the ratio of δ/γ lactones were determined by HPLC. The results are shown in Table 1.

It is understood that the foregoing detailed description is given merely by way of illustration and that modifications and variations may be made therein without departing from the spirit and scope of the invention.

TABLE 1

| Olefin | Olefin Mass (g) | mmoles | Catalyst | Catalyst mL | Catalyst Mass(g) | mmoles | Equiv. |
|---|---|---|---|---|---|---|---|
| Oleic | 10 | 35.46 | HClO4 | 6.43 | 10.71 | 106.38 | 3.0 |
| Oleic | 10 | 35.46 | H2SO4 | 3.73 | 6.96 | 70.92 | 2.0 |
| Oleic | 10 | 35.46 | H2SO4 | 3.73 | 6.96 | 70.92 | 2.0 |
| Oleic | 10 | 35.46 | H2SO4 | 5.60 | 10.43 | 106.38 | 3.0 |
| Oleic | 10 | 35.46 | H2SO4 | 5.60 | 10.43 | 106.38 | 3.0 |
| Oleic | 10 | 35.46 | H2SO4 | 7.46 | 13.91 | 141.84 | 4.0 |
| Oleic | 10 | 35.46 | H2SO4 | 3.73 | 6.96 | 70.92 | 2.0 |
| Oleic | 10 | 35.46 | H2SO4 | 3.73 | 6.96 | 70.92 | 2.0 |
| Oleic | 10 | 35.46 | H2SO4 | 1.87 | 3.48 | 35.46 | 1.0 |
| Oleic | 10 | 35.46 | H2SO4 | 3.73 | 6.96 | 70.92 | 2.0 |
| Oleic | 10 | 35.46 | H2SO4 | 1.87 | 3.48 | 35.46 | 1.0 |
| Oleate* | 10 | 33.78 | H2SO4 | 3.60 | 6.63 | 67.57 | 2.0 |
| Oleate* | 10 | 33.78 | H2SO4 | 3.60 | 6.63 | 67.57 | 2.0 |
| Oleate* | 10 | 33.78 | H2SO4 | 3.60 | 6.63 | 67.57 | 2.0 |
| Oleate* | 10 | 33.78 | H2SO4 | 3.60 | 6.63 | 67.57 | 2.0 |
| Oleic | 10 | 35.46 | pTSA |  | 6.74 | 35.46 | 1.0 |
| Erucic | 10 | 29.54 | H2SO4 | 3.11 | 5.79 | 59.07 | 2.0 |
| Triolein | 10 | 11.31 | H2SO4 | 3.57 | 6.66 | 67.87 | 6.0 |
| Oleic | 10 | 35.46 | H2SO4 | 3.73 | 6.96 | 70.92 | 2.0 |
| Oleic | 10 | 35.46 | H2SO4 | 3.73 | 6.96 | 70.92 | 2.0 |
| Oleic | 10 | 35.46 | H2SO4 | 3.73 | 6.96 | 70.92 | 2.0 |
| Oleic | 10 | 35.46 | H2SO4 | 3.73 | 6.96 | 70.92 | 2.0 |
| Oleic | 100 | 354.47 | H2SO4 | 37.70 | 69.44 | 708.04 | 2.0 |

| Olefin | Solvent | % Solvent | H2O | Temp | Time | δ | γ | Estolide | FA's | Notebook |
|---|---|---|---|---|---|---|---|---|---|---|
| Oleic | CH2Cl2 | 500 | 0 | 40 | 24 | 17.5 | 3.6 | 67.1 | 11.8 | 16231-57 |
| Oleic | None | 0 | 0 | 40 | 24 | 19.9 | 5.8 | 60.6 | 13.8 | 16231-59 |
| Oleic | CH2Cl2 | 500 | 0 | 40 | 24 | 44.3 | 8.6 | 36.9 | 10.2 | 16231-58 |
| Oleic | CH2Cl2 | 500 | 0 | 40 | 24 | 55.8 | 5.4 | 32.9 | 5.9 | 16231-67 |
| Oleic | CH2Cl2 | 600 | 0 | 40 | 24 | 55.0 | 5.2 | 32.6 | 5 | 16231-65 |
| Oleic | CH2Cl2 | 500 | 0 | 40 | 24 | 56.1 | 4.9 | 39.0 | 0 | 16321-60 |
| Oleic | CH2Cl2 | 100 | 0 | 40 | 24 | 59.1 | 8.1 | 24.6 | 8 | 16231-66 |
| Oleic | CH2Cl2 | 100 | 0.1 | 40 | 24 | 15.3 | 11.8 | 65.9 | 7 | 16231-73 |
| Oleic | CH2Cl2 | 500 | AcOH | 40 | 24 | 31.2 | 2.5 | 39.7 | 26.2 | 16231-62 |
| Oleic | CH2Cl2 | 500 | AcOH | 40 | 24 | 6.0 | 19.0 | 55.0 | 19 | 16231-63 |

TABLE 1-continued

| | | | | | | | | | | | |
|---|---|---|---|---|---|---|---|---|---|---|---|
| Oleic | CH2Cl2 | 50 | AcOH | 40 | 24 | 8.6 | 38.0 | 13.5 | | 39.9 | 16231-64 |
| Oleate* | CH2Cl2 | 100 | 0 | 40 | 24 | 52.0 | 5.6 | 40.1 | | 2.3 | 16231-74 |
| Oleate* | CH2Cl2 | 100 | 0.1 | 40 | 24 | 38.7 | 10.4 | 47.1 | | 3.8 | 16231-71 |
| Oleate* | None | 0 | 0.1 | 40 | 24 | 42.8 | 9.4 | 44.0 | | 3.8 | 16231-68 |
| Oleate* | MeOH | 100 | 0.1 | 40 | 24 | 12.0 | 1.0 | 17.0 | | 70 | 16231-69 |
| Oleic | CH2Cl2 | 100 | 0 | 40 | | N.R. Insoluble | | | | | 16103-882 |
| Erucic | CH2Cl2 | 100 | 0 | 40 | 24 | 44.8 | 4.7 | 50.4 | | NA | 16286-884 |
| Triolein | CH2Cl2 | 100 | 0 | 40 | 24 | 38 | 6.7 | 50.8 | | 4.5 | 16286-885 |
| Oleic | CHCl3 | 100 | 0 | 40 | 24 | 54.4 | 5.66 | 35.2 | | 4.77 | 16231-76 |
| Oleic | CHCl3 | 100 | 0 | 50 | 24 | 32.7 | 36 | 26.68 | | 4.62 | 16231-90 |
| Oleic | CHCl3 | 100 | 0 | 60 | 24 | 15.2 | 60 | 22 | | 2.8 | 16231-94 |
| Oleic | CHCl3 | 100 | 0 | 70 | 24 | 7 | 70.3 | 20.7 | | 2 | 16231-95 |
| Oleic | CH2Cl2 | 100 | 0 | 42 | 24 | 80.1 | 9.66 | 6 | | 4.25 | 16231-075 |

*Methyl Ester

We claim:

1. A method for making δ-lactones comprising reacting one or more $\Delta^9$ to $\Delta^{15}$ unsaturated fatty acids in the presence of a catalytically effective amount of acid catalyst selected from the group consisting of $H_2SO_4$, methane sulfonic acid, trifluoromethane sulfonic acid, and mixtures thereof, at a temperature between about 20 to 70° C., optionally in a dipolar, non-participating, non-aqueous solvent having a dielectric constant greater than or equal to about 4.0, and under conditions and for a period of time sufficient to form a δ-lactone of the formula:

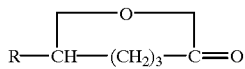

R—CH—(CH$_2$)$_3$—C=O wherein R is a hydrocarbon which may be saturated or unsaturated, or branched or straight chain.

2. The method of claim 1 wherein said solvent is not an aromatic compound.

3. The method of claim 2 wherein the reaction is conducted substantially in the absence of aromatic compounds.

4. The method of claim 1 wherein the volume of said solvent is between about 0 to 600% measured as the volume solvent relative to the weight of fatty acid.

5. The method of claim 4 wherein the volume of said solvent is between about 0 to 200%.

6. The method of claim 5 wherein the volume of said solvent is between about 50 to 200%.

7. The method of claim 6 wherein the volume of said solvent is about 100%.

8. The method of claim 1 wherein said solvent is selected from the group consisting of $CHCl_3$ and $CH_2Cl_2$.

9. The method of claim 1 wherein said catalyst is $H_2SO_4$.

10. The method of claim 1 wherein the amount of said catalyst is between about 0.5 and 10 molar equivalents.

11. The method of claim 10 wherein the amount of said catalyst is between about 1.0 and 4.0 molar equivalents.

12. The method of claim 11 wherein the amount of said catalyst is between about 1.0 to 2.0 molar equivalents.

13. The method of claim 1 wherein the temperature is between about 40 to 70° C.

14. The method of claim 1 wherein said reacting is in a single step.

15. The method of claim 1 wherein the reaction to form said δ-lactones does not introduce any functionalities onto said R group.

16. The method of claim 1 wherein said $\Delta^9$ to $\Delta^{15}$ unsaturated fatty acids are in free form.

17. The method of claim 1 wherein said $\Delta^9$ to $\Delta^{15}$ unsaturated fatty acids are esterified.

18. The method of claim 17 wherein said $\Delta^9$ to $\Delta^{15}$ unsaturated fatty acids are esterified to a hydrocarbon.

19. The method of claim 17 wherein said $\Delta^9$ to $\Delta^{15}$ unsaturated fatty acids are esterified to glycerol as mono-, di-, or triglycerides.

20. The method of claim 1 wherein said $\Delta^9$ to $\Delta^{15}$ unsaturated fatty acids comprise free and esterified unsaturated fatty acids of the formula:

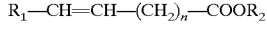

R$_1$—CH=CH—(CH$_2$)$_n$—COOR$_2$ wherein n is an integer between 7 and 13, R$_1$ is hydrocarbon which may be saturated or unsaturated, and branched or straight chain, and R$_2$ is an H, an aliphatic hydrocarbon, or a glyceride moiety which in combination with the fatty acid comprises a mono-, di- or triglyceride.

21. The method of claim 20 wherein n is 7, 9 or 11, and R$_1$ is a C$_4$ to C$_{20}$ hydrocarbon.

22. The method of claim 20 wherein said $\Delta^9$ to $\Delta^{15}$ unsaturated fatty acids are selected from the group consisting of free and esterified palmitoleic acid, oleic acid, linoleic acid, erucic acid, and linolenic acid.

23. The method of claim 20 wherein said $\Delta^9$ to $\Delta^{15}$ unsaturated fatty acids are selected from the group consisting of free and esterified oleic acid.

24. The method of claim 1 further comprising reacting said δ-lactone with an alkali in an aqueous solution for a period of time effective to form a 5-hydroxy fatty acid of the formula:

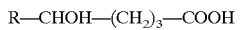

R—CHOH—(CH$_2$)$_3$—COOH wherein R is a hydrocarbon which may be saturated or unsaturated, or branched or straight chain.

* * * * *